United States Patent
Sebring

(10) Patent No.: US 9,532,953 B2
(45) Date of Patent: *Jan. 3, 2017

(54) SOLVENT EXTRACTION FROM BIODEGRADABLE MICROPARTICLES

(71) Applicant: AntriaBio, Inc., Louisville, CO (US)

(72) Inventor: Greg Bryden Sebring, Longmont, CO (US)

(73) Assignee: ANTRIABIO, INC., Louisville, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/974,201

(22) Filed: Dec. 18, 2015

(65) Prior Publication Data

US 2016/0128942 A1 May 12, 2016

Related U.S. Application Data

(62) Division of application No. 14/324,734, filed on Jul. 7, 2014, now Pat. No. 9,439,864.

(51) Int. Cl.
*A61K 38/26* (2006.01)
*A61K 38/28* (2006.01)
(Continued)

(52) U.S. Cl.
CPC .............. *A61K 9/1682* (2013.01); *A61K 9/16* (2013.01); *A61K 9/1647* (2013.01);
(Continued)

(58) Field of Classification Search
CPC .. A61K 38/26; A61K 38/28; A61K 47/48215; A61K 9/16; A61K 9/1647; A61K 9/1682; A61K 9/1694; B01D 11/0415; B01D 11/0492; B01J 13/00
See application file for complete search history.

(56) References Cited

U.S. PATENT DOCUMENTS

| 5,609,886 A | 3/1997 | Wantier et al. |
| 5,654,008 A | 8/1997 | Herbert et al. |

(Continued)

FOREIGN PATENT DOCUMENTS

| WO | 89/03678 A1 | 5/1989 |
| WO | 2016/007468 | 1/2016 |

OTHER PUBLICATIONS

Freitas, S., et al. Microencapsulation by solvent extraction/evaporation: reviewing the state of the art of microsphere preparation process technology, Journal of Controlled Disease, 2005, 102, p. 313-332.

(Continued)

*Primary Examiner* — Ernst V Arnold
(74) *Attorney, Agent, or Firm* — Kilpatrick Townsend & Stockton LLP

(57) ABSTRACT

Embodiments may include a method for reducing a solvent concentration in a plurality of microparticles. The method may involve contacting a mixture including the plurality of microparticles and the solvent with water to form an aqueous suspension. A first portion of the solvent may dissolve into the water of the aqueous suspension to reduce the solvent concentration in the plurality of microparticles from a first solvent concentration in the mixture to a second solvent concentration in the aqueous suspension. The method may also include transferring the aqueous suspension to a concentration unit that may further reduce the solvent concentration from the second solvent concentration to a third solvent concentration. The method may further include transferring a microparticle concentrate with the third solvent concentration to a washing unit to form an amalgam of washed microparticles with a fourth solvent concentration. The method may also include drying the amalgam of washed microparticles.

9 Claims, 4 Drawing Sheets

(51) Int. Cl.
    *A61K 9/16*       (2006.01)
    *B01J 13/00*     (2006.01)
    *A61K 47/48*    (2006.01)
    *B01D 11/04*    (2006.01)

(52) U.S. Cl.
    CPC ............ *A61K 9/1694* (2013.01); *A61K 38/26* (2013.01); *A61K 38/28* (2013.01); *A61K 47/48215* (2013.01); *B01D 11/0415* (2013.01); *B01D 11/0492* (2013.01); *B01J 13/00* (2013.01)

(56) References Cited

U.S. PATENT DOCUMENTS

| | | |
|---|---|---|
| 5,792,477 A | 8/1998 | Rickey et al. |
| 6,123,848 A | 9/2000 | Quepons Dominquez et al. |
| 6,270,802 B1 * | 8/2001 | Thanoo ................ A61K 9/1647 264/4.1 |
| 9,040,664 B2 | 5/2015 | Hinds et al. |
| 2007/0083006 A1 | 4/2007 | Hinds et al. |
| 2007/0190154 A1 | 8/2007 | Zeigerson |
| 2007/0207211 A1 | 9/2007 | Zeigerson |
| 2008/0317865 A1 | 12/2008 | Trapani et al. |
| 2010/0063179 A1 * | 3/2010 | Atkinson ............. A61K 9/5031 523/332 |
| 2016/0000713 A1 | 1/2016 | Sebring et al. |

OTHER PUBLICATIONS

International Search Report and Written Opinion of PCT/US2015/039316 mailed on Oct. 16, 2015, all pages.

O'Donnell, P.B. et al. Preparation of microspheres by the solvent evaporation technique, Advanced Drug Delivery Reviews, 1997, 28, p. 25-42.

* cited by examiner

SOLVENT EXTRACTION FROM BIODEGRADABLE MICROPARTICLES

CROSS-REFERENCES TO RELATED APPLICATIONS

This application is a divisional of copending U.S. patent application Ser. No. 14/324,734 entitled "SOLVENT EXTRACTION FROM BIODEGRADABLE MICROPARTICLES" and filed Jul. 7, 2014.

BACKGROUND

Biodegradable microparticles may be used to deliver drugs, hormones, proteins, and other medically active agents to a patient. As they degrade, the microparticles may gradually release agents to the body intravenously or subcutaneously and may be administered to the body with a needle. Biodegradable microparticles may reduce the frequency of injections, as the agents are released gradually into the body. The microparticle size distribution and flowability characteristics affect the gauge and other characteristics of the needle. More flowable microparticles may be easier to fill into vials and may be more easily injected with a large gauge (smaller diameter) needle. Once in the body, the rate of release and the concentration of the medically active agent may be related to the microparticle size, the microparticle size distribution, the initial concentration of the medically active agent, and other characteristics of the microparticles. Such biodegradable microparticles also need to meet health and safety regulations for contaminant concentrations including the solvents used to prepare the microparticles. Thus, a need for microparticles with superior syringability, injectability, flowability, uniformity, and purity characteristics exists. The methods and systems described herein provide solutions to these and other needs.

BRIEF SUMMARY

Solvents are often used during the preparation of biodegradable microparticles. Initially, these solvents are at concentrations that are higher than levels safe for injection into a patient. The solvent concentration in the microparticles can be reduced by extracting the solvent with a liquid, such as water. The solvent extraction may be split between multiple steps or units, which may reduce the amount of water required for solvent reduction. For example, an extraction method or system may include two steps or tanks. Additionally, an extraction method or system may include a cross flow filtration column, which may reduce the solvent concentration and concentrate the amount of microparticles in a suspension. Microparticles may then be rinsed with an inorganic base and dried. This method or system may provide microparticles with low solvent concentrations and superior characteristics for administering to a patient.

Embodiments of the present technology may include a method for reducing a solvent concentration in a plurality of microparticles. The method may involve contacting a mixture including the plurality of microparticles and the solvent with water, and this contact may form an aqueous suspension. A first portion of the solvent may dissolve into the water of the aqueous suspension to reduce the solvent concentration in the plurality of microparticles from a first solvent concentration in the mixture to a second solvent concentration in the aqueous suspension. The method may also include transferring the aqueous suspension to a concentration unit that may further reduce the solvent concentration in the plurality of microparticles from the second solvent concentration to a third solvent concentration. The reduction to the third solvent concentration may include introducing additional water to the aqueous suspension in the concentration unit. The reduction may also include removing at least a portion of the water and at least a portion of the solvent from the aqueous suspension in the concentration unit. In the concentration unit, additional water may be introduced at a slower rate than the water and the solvent are removed from the concentration unit to form a microparticle concentrate with the third solvent concentration. The method may further include transferring the microparticle concentrate to a washing unit, where the microparticle concentrate may be contacted with a washing solution to form an amalgam of washed microparticles with a fourth solvent concentration. The method may also include drying the amalgam of washed microparticles to form the plurality of microparticles with a reduced solvent concentration. These operations may work together to reduce the solvent concentration in the microparticles from the first solvent concentration to the reduced solvent concentration.

Embodiments may also include a system for reducing a solvent concentration in a plurality of microparticles. The system may include a solvent extraction tank. In the solvent extraction tank, a mixture including the plurality of microparticles and the solvent may be contacted with water to form an aqueous suspension. A first portion of the solvent may dissolve into the water of the aqueous suspension to reduce the solvent concentration in the plurality of microparticles from a first solvent concentration in the mixture to a second solvent concentration in the aqueous suspension. The system may also include a concentration unit in fluid communication with the solvent extraction tank. The concentration unit may further reduce the solvent concentration in the plurality of microparticles from the second solvent concentration to a third solvent concentration. This reduction may include introducing additional water to the aqueous suspension in the concentration unit. The reduction may also include removing at least a portion of the water and at least a portion of the solvent from the aqueous suspension in the concentration unit. The additional water may be introduced at a slower rate than the water and the solvent are removed from the concentration unit. A microparticle concentrate with the third solvent concentrate may be formed. The system may further include a washing unit adapted to receive the microparticle concentration from the concentration unit. In the washing unit, the microparticle concentrate may be contacted with a washing solution and may form an amalgam of washed particles with a fourth solvent concentration.

Embodiments may further include a method of preparing a plurality of biodegradable microspheres with a medically active agent, where the biodegradable microspheres have a reduced level of a preparation solvent. The method may include contacting a mixture including the plurality of biodegradable microspheres and the preparation solvent with water, which may form an aqueous suspension. A first portion of the preparation solvent may dissolve into the water of the aqueous suspension and may reduce the solvent concentration in the plurality of biodegradable microspheres from a first solvent concentration in the mixture to a second solvent concentration in the aqueous suspension. The method may also include transferring the aqueous suspension to a concentration unit that further reduces the solvent concentration in the plurality of biodegradable microspheres from the second solvent concentration to a third solvent concentration. This reduction may include introducing additional water to the aqueous suspension in the concentration unit. The reduction may also include removing at least a portion of the water and at least a portion of the preparation solvent from the aqueous suspension in the concentration unit. The additional water may be introduced at a slower rate than the water and the solvent are removed from the concentration unit to form a biodegradable microsphere concentrate with the third solvent concentration. The method may further include transferring the biodegradable microsphere concentrate to a washing unit, where the biodegradable microsphere concentrate is contacted with a washing solution to form an amalgam of washed biodegradable microspheres with a fourth solvent concentration. The method may also include drying the amalgam of washed biodegradable microspheres to form the plurality of biodegradable microspheres with a reduced solvent concentration. These operations may work together to reduce the solvent concentration from the first solvent concentration in the mixture to the reduced solvent concentration in the plurality of biodegradable microspheres.

Embodiments may also include a composition that can be dried with a vacuum unit into a powder for filling a syringe. The composition may include a plurality of biodegradable microspheres, where the plurality of biodegradable microspheres may include a medically activated agent. In these or other embodiments, the composition may also include a solvent at a concentration of 0.03 wt. % or less. The composition may further include a washing solution that includes an inorganic base. The inorganic base may have a concentration of 0.1 to 1 w/w %.

Biodegradable microspheres may be loaded into a vial before being mixed with a diluent and administered to a patient. Repeatable, controlled loadings for medical treatment may may result from biodegradable microspheres that are dry, are in powder form, have good flowability, and have a low impurity content. The methods and systems of the present technology may produce a microsphere powder with good flowability characteristics. The solvent extraction steps may remove impurities below regulated levels, and the method may include a drying process to remove water from the microspheres. Superior flowability may be achieved through reducing microsphere clumping and aggregation by rinsing the microspheres with an inorganic base.

Additionally, any process to produce flowable, injectable, and syringeable biodegradable microspheres should be efficient and minimize degradation of the medically active agent. The combination of solvent extraction and drying steps reduces the amount of water needed to be added to the microspheres to extract the solvent. Reducing water usage reduces input and utility costs and also reduces waste. At the same time, methods and systems of the present technology may also reduce processing time and temperature, which may reduce degradation of the medically active agent or microparticles. Embodiments of the present technology provide these and additional benefits.

BRIEF DESCRIPTION OF THE DRAWINGS

Embodiments of the present technology are described in conjunction with the appended figures.

DETAILED DESCRIPTION

Conventional methods for extracting solvent from medicinal microspheres typically include using high temperatures to evaporate out the solvent. Applying heat, however, may degrade the microsphere or the medically active agent. Applying heat may also generate solvent fumes, and these fumes may be harmful to human health and subject to emissions regulations.

The solvent can also be removed by extracting it from the microspheres with water. Slightly polar solvents are slightly soluble in water. For instance, methylene chloride is slightly polar and is slightly soluble in water. Furthermore, the partition coefficient (i.e., the ratio of the concentration of the solvent in the microspheres to the concentration of the solvent in water) is normally a constant at constant temperature. Methylene chloride, for example, has a partition coefficient of about 18 at room temperature (i.e., 20° C.). Consequently, a solvent could be removed from microspheres to below a requisite level in one step with a sufficient volume of water. However if the initial concentration of methylene chloride was 15% and was reduced in one step to the 300 ppm concentration considered safe for human injection, almost 9,000 L of water per liter of a microsphere suspension would be required. Dividing up the extraction process into multiple steps would decrease the amount of water required but also increase the number of unit operations, such as vessels and pumps. Extraction in a plug flow reactor, such as in a cross-flow filtration (CFF) column, would reduce the number of unit operations but would increase the residence time needed to complete the extraction. Increasing the residence time may degrade the microspheres or the medically active agents. In short, extracting the solvent may lead to tradeoffs between the amount of water, the number of unit operations, and/or the residence time for the extraction. The present technology provides a balance between these tradeoffs while producing microparticles with superior characteristics.

Figure 1:
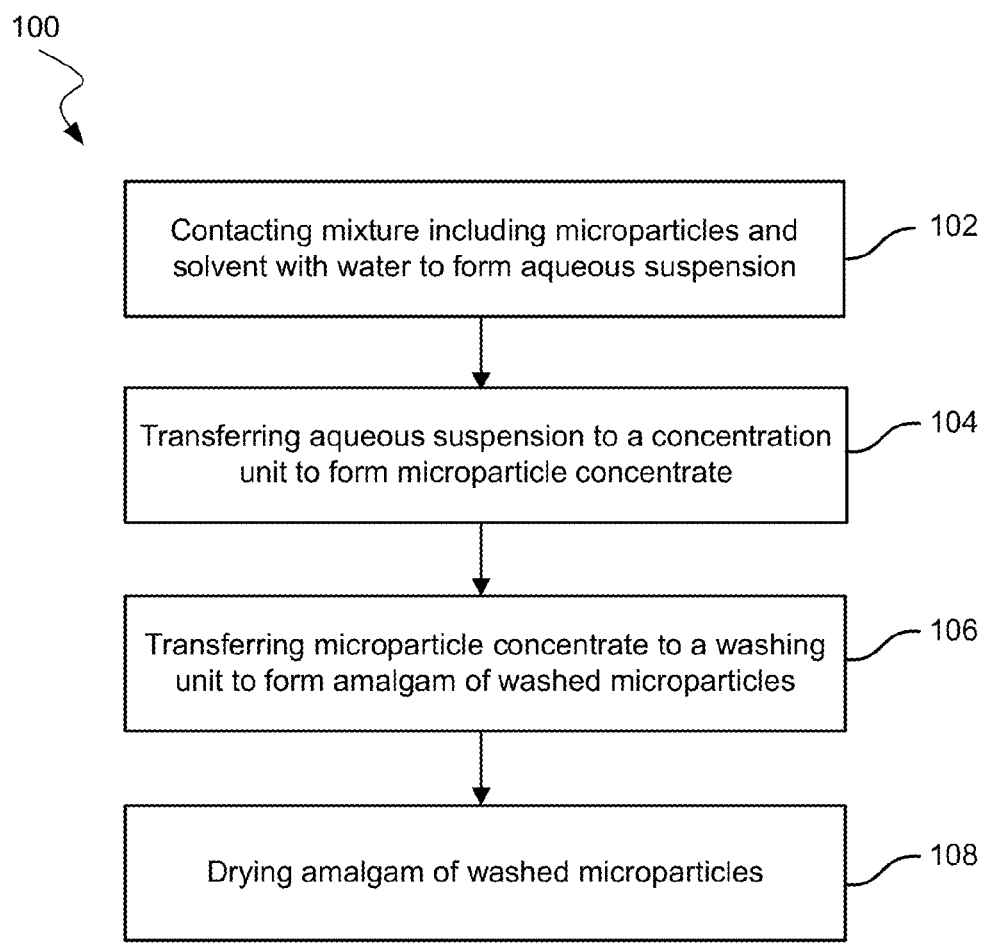
FIG. 1 shows a method for reducing a solvent concentration in a plurality of microparticles according to embodiments.

As shown in FIG. 1, embodiments may include a method 100 for reducing a solvent concentration in a plurality of microparticles. The microparticles may include biodegradable microspheres that contain a medically active agent. For example, the medically active agent may include a protein, such as insulin or glucagon-like peptide 1 (GLP-1) protein, that is medically active in a patient's body. Other medically active agents include, but are not limited to, insulin analogs (i.e., insulin with one or several amino acids replaced by other amino acids), peptide hormones, insulin derivatives (i.e., insulin conjugated to carrier proteins, such as antibodies, antibody fragments, biopolymers, etc.), polynucleotides and their derivatives, polynucleosides and their derivatives, small molecule therapeutics that are hydrophobic or amphiphilic, biologics, proteins, peptides, and mixtures thereof.

When the microspheres are subcutaneously injected into a patient, the medically active agent is gradually released by the dissolving microspheres. The gradual release of the medically active agent can increase the time between injections, resulting in a lower injection frequency. When the medically active agent includes insulin, the insulin may be PEGylated by covalently attaching polyethylene glycol units to certain reactive amino groups on the insulin. PEGylated insulin is described in U.S. application Ser. No. 10/553,570, which is incorporated herein by reference. In addition, the biodegradable microspheres may include poly(lactic-co-glycolic) acid (PLGA). PLGA is an FDA-approved polymer for administration into the human body. PLGA may degrade into lactic acid and glycolic acid, both of which can be safely metabolized by the human body. In some embodiments, the solvent in the microparticles may include a halogenated organic solvent. For instance, the halogenated organic solvent may include methylene chloride.

The microspheres may include a plurality of medically active agents. The plurality of medically active agents may include drugs, proteins, and other compounds in embodiments. A single microsphere may include the plurality of medically active agents. Alternatively, a first plurality of microspheres may include a first medically active agent, and a second plurality of microspheres may include a second medically active agent. A third plurality of microspheres may include a third medically active agent, and so on. The total amount of the first medically active agent may be the same as the total amount of the second medically active agent, whether or not each medically active agent is present in the same microsphere. The total amount of the first medically active agent may be different than the total amount of the second medically active agent, whether or not each medically active agent is present in the same microsphere. Each medically active agent may have the same or different release times. The microspheres may include microspheres made from different biodegradable materials.

Method 100 may involve contacting a mixture including the plurality of microparticles and the solvent with water and may form an aqueous suspension 102. Forming the aqueous suspension may harden the microparticles so as to reduce the amount of the medically active agent that may otherwise dissolve into the water of the aqueous suspension. A first portion of the solvent may dissolve or be extracted into the water of the aqueous suspension to reduce the solvent concentration in the plurality of microparticles from a first solvent concentration in the mixture to a second solvent concentration in the aqueous suspension. The first solvent concentration in the mixture may be between 1 and 50 wt. %, between 5 and 25 wt. %, or between 10 and 20 wt. % (e.g., 15 wt. %). The second solvent concentration in the suspension may be between 1 and 10 wt. %, between 1 and 5 wt. %, or about 2 wt. %.

Along with contacting the microparticle mixture with water, method 100 may include transferring the aqueous suspension to a concentration unit 104 that may further reduce the solvent concentration in the plurality of microparticles from the second solvent concentration to a third solvent concentration. In some embodiments, the concentration unit may include a cross-flow filtration unit that may remove water and the solvent from the concentration unit without removing the microparticles. The reduction to the third solvent concentration may include introducing additional water to the aqueous suspension in the concentration unit. The reduction may also include removing at least a portion of the water and at least a portion of the solvent from the aqueous suspension in the concentration unit. In the concentration unit, additional water may be introduced at a slower rate than the water and the solvent are removed from the concentration unit to form a microparticle concentrate with a third solvent concentration. The third solvent concentration in the microparticle concentrate may be about 0.5 wt. %. The microparticle concentrate may include about 1 vol. % or more of the microspheres.

In embodiments, method 100 may further include transferring the microparticle concentrate to a washing unit 106, where the microparticle concentrate may be contacted with a washing solution to form an amalgam of washed microparticles with a fourth solvent concentration. The fourth solvent concentration in the amalgam of washed microparticles may less than or equal to 1 wt. %, less than or equal to 0.1 wt. %, or be less than or equal to 0.03 wt. % (i.e., 300 ppm). The washing solution may include an inorganic base. This inorganic base may include hydroxides or carbonates. For instance, the inorganic base may be sodium hydroxide or sodium bicarbonate. The concentration of the inorganic base may be from 0.1 to 10 w/w % or from 0.1 to 1.0 w/w %. Without intending to be bound by a particular theory, adding an inorganic base to the microsphere is believed to deprotonate molecules on the microspheres and leave the microspheres with a negative charge. The negatively charged microspheres may provide a repulsive force that counteracts the attractive forces that favor agglomeration of the microspheres.

The washing unit may also separate a first group of microparticles having a target diameter from a second group of microparticles having a size outside the target diameter. The target diameter may range from 10 µm to 90 µm, 20 µm to 70 µm, or 25 µm to 63 µm according to embodiments. The mean diameter of the microparticles may be between 30 µm and 50 µm, between 30 µm and 40 µm, or about 38 µm. The separation of the first group from the second group may include the stack of porous screens in the washing unit. The microparticles may include some particles with diameters smaller than the lower target diameter of 25 µm, depending on the efficiency of the separation. Microparticles with diameters smaller than the lower target diameter may total less than 5 vol. %, less than 2 vol. %, or less than 1 vol. % of the total number of microparticles.

Additionally, method 100 may include drying the amalgam of washed microparticles 108 and may form the plurality of microparticles with a reduced solvent concentration. The reduced solvent concentration may be less than or equal to the fourth solvent concentration. A higher amount of solvent in the microparticles at the beginning of the drying operation may be more likely to result in aggregated microparticles in the dryer. Therefore, most solvent concentration reduction should occur before drying. These operations of method 100 may work together to reduce the solvent concentration from the first solvent concentration to the reduced solvent concentration.

Figure 2:
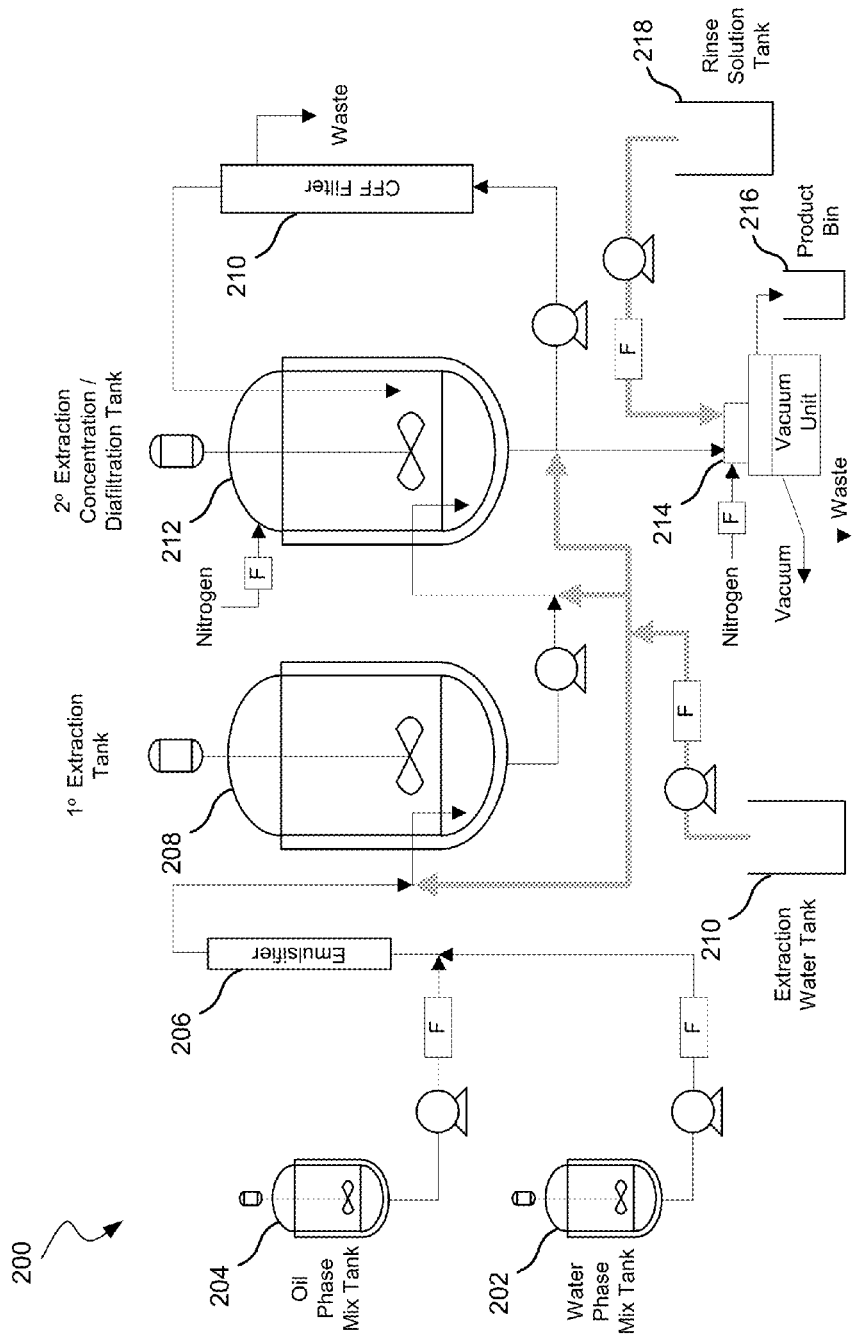
FIG. 2 shows a process flow diagram of a system for reducing a solvent concentration in a plurality of microparticles according to embodiments.

Embodiments may also include a system for reducing a solvent concentration in a plurality of microparticles. FIG. 2 shows an example system 200. A water phase mix tank 202, oil phase mix tank 204, and emulsifier 206 produce microparticles or microspheres. Microparticles or microspheres may be produced by other means as well and may be any of the microparticles or microspheres discussed in this specification. Similarly, the solvent may be any solvent described herein.

The microparticles may be added to solvent extraction tank 208. In solvent extraction tank 208, a mixture including the plurality of microparticles and the solvent may be contacted with water to form an aqueous suspension. Solvent extraction tank 208 may include a mixer to keep the microparticles in the aqueous solution from settling to the bottom of solvent extaction tank 208. The mixing speed may be decreased to minimize foam formation. The water may come from an extraction water tank 210. A first portion of the solvent may dissolve or be extracted into the water of the aqueous suspension to reduce the solvent concentration in the plurality of microparticles from a first solvent concentration in the mixture to a second solvent concentration in the aqueous suspension.

System 200 may also include a concentration unit in fluid communication with solvent extraction tank 208. The concentration unit may further reduce the solvent concentration in the plurality of microparticles from the second solvent concentration to a third solvent concentration. This reduction may include introducing additional water to the aqueous suspension in the concentration unit. The reduction may also include removing at least a portion of the water and at least a portion of the solvent from the aqueous suspension in the concentration unit. The additional water may be introduced at a slower rate than the water and the solvent are removed from the concentration unit. A microparticle concentrate with the third solvent concentration may be formed.

The concentration unit may include a cross-flow filtration column 210 in fluid communication with a second solvent extraction tank 212. Cross-flow filtration column 210 may remove a portion of the water and a portion the solvent from the second solvent extraction tank 212 without removing the microparticles. The waste stream may include solvent at a concentration in the water that would be low enough to go to a conventional wastewater treatment facility. For instance, the waste stream may include about 1.7% of methylene chloride or between 0.03% and 1.4% methylene chloride. Often, wastewater treatment facility limits are based on absolute amounts and not concentrations. With processing at large scales, the solvent may be collected onto activated charcoal beds, which may then be transported to a recycling site.

System 200 may further include a washing unit adapted to receive the microparticle concentration from the concentration unit. In the washing unit, the microparticle concentrate may be contacted with a washing solution and may form an amalgam of washed particles with a fourth solvent concentration. The washing solution may be any washing solution described herein. The washing unit may include a stack of porous screens, which may separate a first group of microparticles having a target diameter from a second group of microparticles having a size outside the target diameter. The target diameter may be any target diameter discussed herein.

The washing unit may also include a vacuum unit 214 to evaporate the water and the solvent from the amalgam washed microparticles to form dried microparticles with a reduced solvent concentration. The washing unit may further include a dry gas supply to carry vapor of the water and the solvent to vacuum unit 214. The dry gas supply may include, for example, dry nitrogen gas, an inert gas, or a gas or mixture of gases substantially without oxygen. System 200 may also include a product bin 216 to receive the dried microparticles with the reduced solvent concentration. In these or other embodiments, system 200 may further include a drying unit adapted to receive the amalgam of washed microparticles from the washing unit a dry the amalgam to form dried microparticles with a reduced solvent concentration. The solvent concentrations in system 200 may be the same or different concentrations as the solvent concentrations discussed herein.

Figure 3:
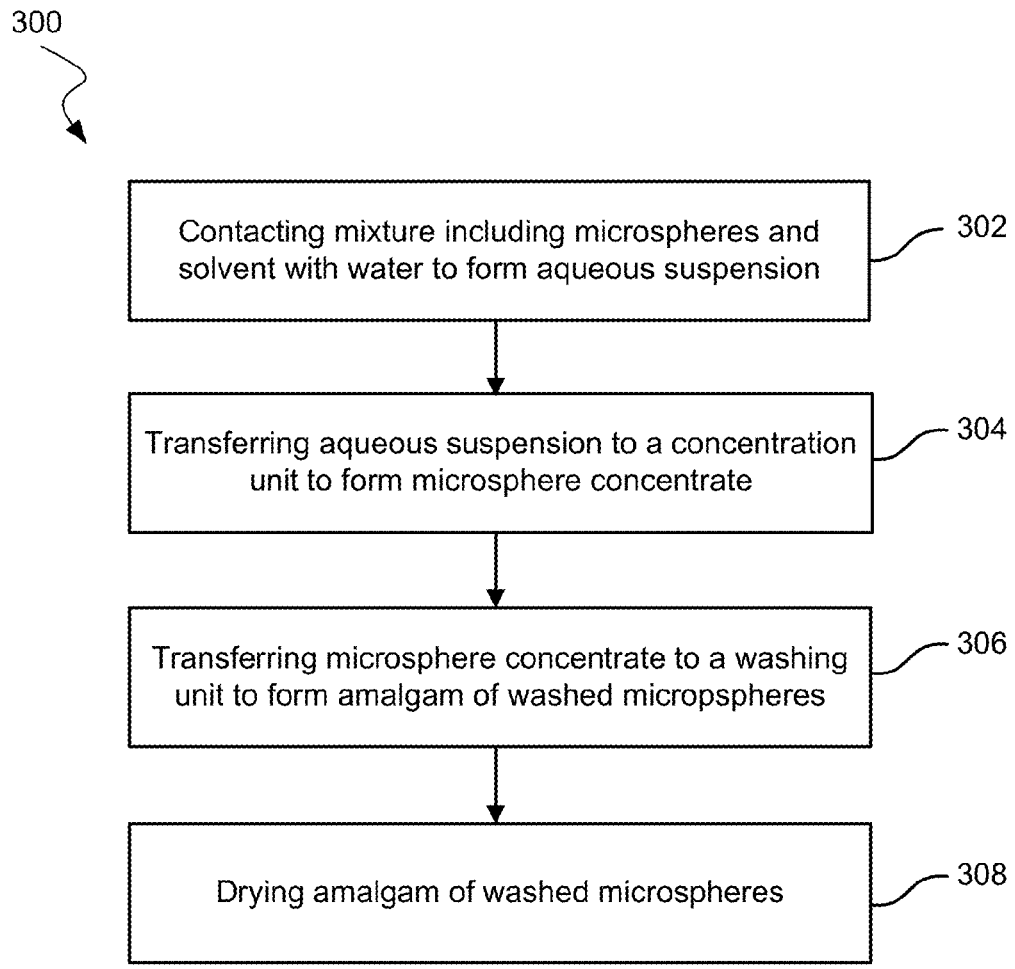
FIG. 3 shows a method of preparing a plurality of biodegradable microspheres according to embodiments.

FIG. 3 shows an example of a method 300 of preparing a plurality of biodegradable microspheres with a medically active agent, where the biodegradable microspheres have a reduced level of a preparation solvent. The microspheres, medically active agent, and the preparation solvent may be any discussed herein. Method 300 may include contacting a mixture including the plurality of biodegradable microspheres and the preparation solvent with water, which may form an aqueous suspension 302. A first portion of the preparation solvent may dissolve into the water of the aqueous suspension and may reduce the solvent concentration in the plurality of biodegradable microspheres from a first solvent concentration in the mixture to a second solvent concentration in the aqueous suspension.

Additionally, method 300 may include transferring the aqueous suspension to a concentration unit 304 that further reduces the solvent concentration in the plurality of biodegradable microspheres from the second solvent concentration to a third solvent concentration. This reduction may include introducing additional water to the aqueous suspension in the concentration unit. The reduction may also include removing at least a portion of the water and at least a portion of the preparation solvent from the aqueous suspension in the concentration unit. The additional water may be introduced at a slower rate than the water and the solvent are removed from the concentration unit to form a biodegradable microsphere concentrate with the third solvent concentration.

Furthermore, method 300 may include transferring the biodegradable microsphere concentrate to a washing unit 306, where the biodegradable microsphere concentrate is contacted with a washing solution to form an amalgam of washed biodegradable microspheres with a fourth solvent concentration. The first, second, third, and fourth solvent concentrations may be the same or different as the concentrations described herein. Likewise, the washing solution may be any washing solution discussed herein.

Method 300 may also include drying the amalgam washed biodegradable microspheres 308 to form the plurality of biodegradable microspheres with a reduced solvent concentration. These operations may work together to reduce the solvent concentration from the first solvent concentration in the mixture to the reduced solvent concentration in the plurality of biodegradable microspheres.

Embodiments may also include a composition that can be dried with a vacuum unit into a powder for filling a syringe. The composition may include a plurality of biodegradable microspheres, where the plurality of biodegradable microspheres may include a medically activated agent. In these or other embodiments, the composition may also include a solvent (e.g., methylene chloride) at a concentration of 0.03 wt. % or less or any concentration discussed herein. The composition may further include a washing solution that includes an inorganic base. The inorganic base may have a concentration of 0.1 to 1 w/w % or any concentration discussed herein. The microspheres, medically activated agent, solvent, washing solution, and inorganic base may be the same as what has been previously described herein. The composition may further include nitrogen gas, an inert gas, or any gas or mixture of gases substantially devoid of oxygen. The composition may be present in a washing unit or a dryer.

The powder of dried microspheres may be filled into a vial, syringe, or other container. The powder may then be mixed with a carrier liquid to form an injectable suspension that can be injected by syringe into a patient. The powder and the carrier liquid may be mixed just prior to injection. The powder and the carrier liquid may each be in one barrel of a dual barrel syringe, or they may be in a single barrel of a single barrel syringe. The carrier liquid may be a biocompatible liquid, which may include water. This carrier liquid may be isotonic and reduce damage to tissues near the injection site. The carrier liquid may include water and may include preservatives. These preservatives may prevent or reduce microbial growth and the also maintain microsphere suspension over the period of time associated with its potential use. The carrier liquid may not affect the release kinetics of the microspheres. Furthermore, the carrier liquid may include a surfactant, which may allow the microspheres to disperse more readily. The carrier liquid may wet the microspheres, which include infiltrating pores at the surface of the microspheres. The wetted microspheres may then be injected in a patient, where they degrade and gradually release a medically active agent. After the medically active agent is released, another dose of wetted microspheres may be injected again into the patient at some duration. This duration may be a week or longer than a week.

EXAMPLE 1

With returning reference to FIG. 2, an emulsion of microspheres containing PEGylated insulin was produced with water phase mix tank 202, oil phase mix tank 204, and emulsifier 206. The ratio of the water phase to the oil phase varied from 1:1 to 2.5:1. For the emulsion with a 1:1 ratio of water phase to oil phase, the methylene chloride concentration was 50%. For the emulsion with a 2.5:1 ratio, the methylene chloride concentration was 28%. The emulsion was sent to the primary extraction tank 208, where it was mixed continuously with sterile filtered extraction water from an extraction water tank 210 at a ratio of 5.6 L extraction water per liter of emulsion as it entered the tank. Primary extraction tank 208 was mixed to maintain a homogeneous suspension during the primary and secondary extraction steps.

The primary extraction suspension was pumped from primary extraction tank 208 to secondary extraction tank 212 at a flow rate of 0.25 L/min. The primary extraction suspension was combined in-line with additional extraction water at a ratio of 4.8 L extraction water per liter primary extraction suspension prior to entering secondary extraction tank 212. In secondary extraction tank 212, the microspheres were continuously being concentrated. Secondary extraction tank 212 was mixed to maintain a homogeneous suspension.

As microspheres were added to secondary extraction tank 212, the suspension was pumped out of the tank through cross-flow filtration (CFF) filter 210 and back into the tank at a flow rate equivalent to a linear velocity of 43 cm/sec through the CFF tubes. Restricting the flow returning to secondary extraction tank 212 applied pressure to the CFF 210. A small fraction of the circulating flow was filtered out through the ceramic CFF membrane to waste, while microspheres were retained in the circulating stream. The flow rate of the waste stream varied from 1 L/min to 6.3 L/min. The concentration of the methylene chloride in the waste stream ranged from 0.03% to 1.4%. The waste stream was sent to a municipal wastewater system. At the scale of this example and at a scale 10-times larger, the waste stream can be disposed in a typical municipal wastewater system. Water was filtered out via CFF 210 at the same rate as water and microspheres were added to the secondary extraction tank, maintaining a constant working volume inside secondary extraction tank 212. The microsphere concentration process was continued until all microspheres had been added to secondary extraction tank 212.

Concentration was continued without additional feed to reduce the extraction bath volume and to achieve a microsphere concentration of 1.0% (feed mass/volume). Once the appropriate volume was reached, freshwater was fed to secondary extraction tank 212 as wastewater was removed via CFF 210 at the same rate to maintain a constant volume. Water was exchanged at a rate of 15 minutes per diavolume or full exchange of the working volume (e.g., 1 L/min for a 15 L working volume). Extraction water tank 210 and secondary extraction tank 212 were heated from 22° C. to 35° C. for over 60 minutes and held at 35° C. to aid in solvent extraction.

After 8.5 diavolumes of water exchange, feed and filtrate flows were stopped. In order to recover the microspheres from the CFF loop, water was fed directly to the loop inlet from extraction water tank 210. A volume of water equal to twice the CFF system hold-up volume was pumped through the loop and into secondary extraction tank 212 so all microspheres were collected in the secondary extraction tank 212. After holding the microspheres at 35° C. for one hour to complete solvent extraction, the entire bath was cooled to 5° C.

After the microsphere bath reached the final temperature of 5° C., the secondary extraction suspension was transferred to the SWECO™ vibratory separator/dryer 214 by pressurizing secondary extraction tank 212 and loading microspheres into the dryer through a top port. While the dryer was vibrating, the suspension gravity drains through a scalping, or top, screen with spacing of 63 µm. A product, or bottom, screen catches the remaining microspheres larger than 25 µm, allowing liquid and undersized microspheres to fall through a waste drain.

Aqueous sodium bicarbonate was added in a SWECO™ rinse solution tank 218 at a concentration of 0.5% w/w in a minimum volume of 2.2 L per 100 g feed. The solution was mixed to dissolve the sodium bicarbonate and simultaneously cooled to 5° C. After the entire secondary extraction bath was fed to the dryer, the dryer's drain was closed. Rinse solution from rinse solution tank 218 was fed to the dryer and held for a minimum of 30 seconds. The rinse solution was drained, the process was repeated for a second time.

The dryer was then allowed to drain until only a wet cake remained on the screens (i.e., no standing liquid). The dryer was then isolated from any vent and supply lines, and vacuum was pulled via the drain port to evaporate the water from the wet cake. A dry nitrogen purge was fed to the top of the dryer to displace the water vapor. Vibration was continuously present throughout the entire process, including during loading, rinsing, and drying. After drying, the dryer product plug was opened, allowing the microspheres to flow into product bin 216.

EXAMPLE 2

Example 1 was repeated with an emulsion of microspheres containing non-PEGylated insulin instead of PEGylated insulin.

EXAMPLE 3

Example 1 was repeated with an emulsion of microspheres containing GLP-1 protein instead of PEGylated insulin.

EXAMPLE 4

Example 1 was repeated with an emulsion containing two different medically active agents.

EXAMPLE 5

Microspheres were treated with an aqueous sodium bicarbonate solution and compared to untreated microspheres.

Figure 4A:
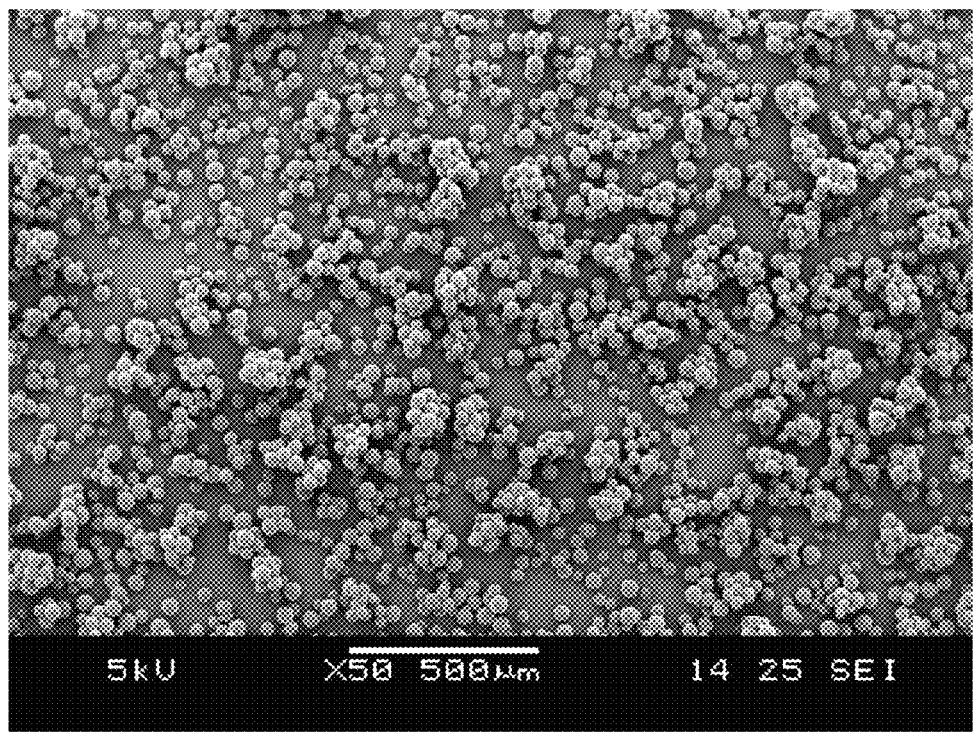
FIG. 4A shows a scanning electron microscope (SEM) image of dried microspheres not treated with a sodium bicarbonate solution.
Figure 4B:
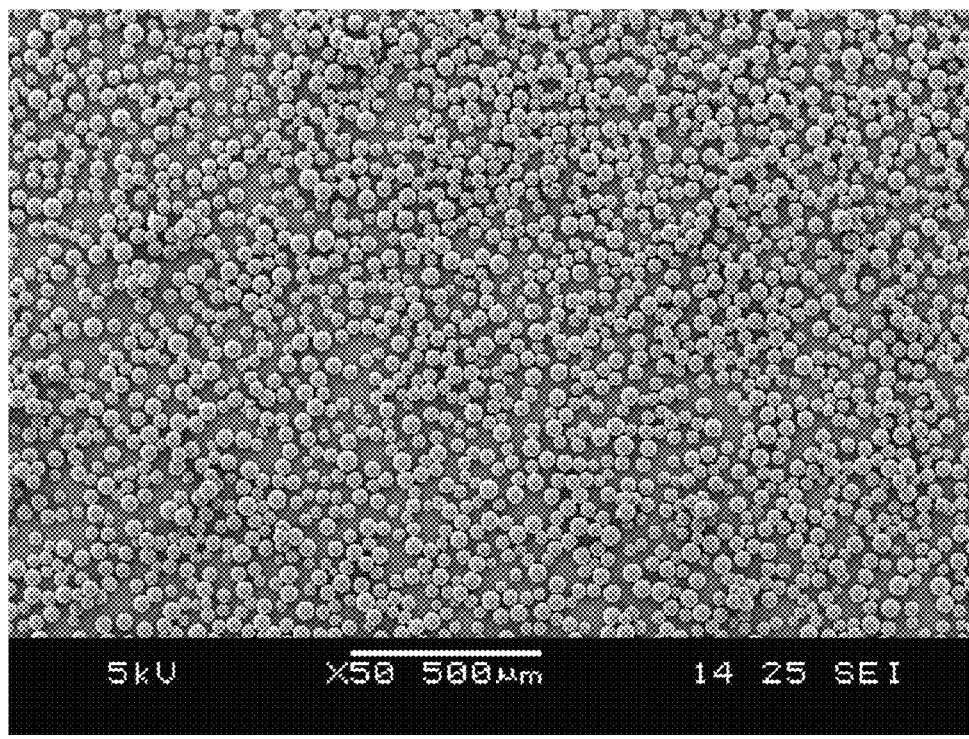
FIG. 4B shows a SEM image of dried microspheres treated with a sodium bicarbonate solution.

The treated microspheres were rinsed three times with a chilled 0.5% sodium bicarbonate solution. Both the treated and untreated microspheres were dried for 2.5 hours and then vibrated in the SWECO™ dryer for 13 hours at atmospheric pressure. Hard clumps of sizes up to 3 mm formed in the untreated microsphere batch, as shown in the SEM image in FIG. 4A. Far fewer and smaller clumps formed in the treated portion, as shown in the SEM image in FIG. 4B. This example shows the reduced aggregation of microspheres after rinsing with a sodium bicarbonate solution.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific embodiment may not always be present in variations of that embodiment or may be added to other embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the microsphere" includes reference to one or more microspheres and equivalents thereof known to those skilled in the art, and so forth. The invention has now been described in detail for the purposes of clarity and understanding. However, it will be appreciated that certain changes and modifications may be practice within the scope of the appended claims.

What is claimed is:

1. A method for reducing a solvent concentration in a plurality of microparticles, the method comprising:
   transferring an aqueous suspension to a concentration unit, wherein:
      the aqueous suspension comprises a plurality of microparticles, a solvent, and water,
      the plurality of microparticles has a first solvent concentration, and
      a first portion of the solvent is dissolved in the water;
   introducing additional water to the aqueous suspension in the concentration unit;
   removing a second portion of the water and a portion of the solvent from the aqueous suspension in the concentration unit to form a microparticle concentrate with a second solvent concentration, wherein:
      the additional water is introduced at a slower rate than the water and the solvent are removed from the concentration unit, and
      the second solvent concentration is less than the first solvent concentration.

2. The method of claim 1, further comprising forming the aqueous suspension by contacting a mixture comprising the plurality of microparticles and the solvent with water.

3. The method of claim 1, further comprising transferring the microparticle concentrate to a washing unit, wherein the microparticle concentrate is contacted with a washing solution to form an amalgam of washed microparticles with a third solvent concentration.

4. The method of claim 3, wherein the third solvent concentration is 0.03 wt. % or less.

5. The method of claim 3, wherein:
   the first solvent concentration is 1 to 5 wt. %, and
   the third solvent concentration is 0.03 wt. % or less.

6. The method of claim 1, further comprising separating a first group of microparticles having a target diameter range from a second group of microparticles having a size outside the target diameter range.

7. The method of claim 3, further comprising drying the amalgam of washed microparticles to form the plurality of microparticles with a reduced solvent concentration.

8. The method of claim 1, wherein the microparticles comprise biodegradable microspheres that contain a medically active agent.

9. The method of claim 1, wherein the solvent in the microparticles comprises a halogenated organic solvent.

* * * * *